United States Patent
Yang et al.

(10) Patent No.: US 10,422,733 B2
(45) Date of Patent: Sep. 24, 2019

(54) METHOD AND DEVICE FOR TESTING WETTABILITY OF DENSE OIL RESERVOIR

(71) Applicant: PetroChina Company Limited, Beijing (CN)

(72) Inventors: Zhengming Yang, Beijing (CN); Yutian Luo, Beijing (CN); Xuewu Wang, Beijing (CN); Xuewei Liu, Beijing (CN); Shengchun Xiong, Beijing (CN); Yapu Zhang, Beijing (CN); Ying He, Beijing (CN)

(73) Assignee: PetroChina Company Limited, Beijing (CN)

( * ) Notice: Subject to any disclaimer, the term of this patent is extended or adjusted under 35 U.S.C. 154(b) by 221 days.

(21) Appl. No.: 15/490,231

(22) Filed: Apr. 18, 2017

(65) Prior Publication Data

US 2018/0088016 A1   Mar. 29, 2018

(30) Foreign Application Priority Data

Sep. 26, 2016  (CN) .......................... 2016 1 8529775

(51) Int. Cl.
*G01V 3/00* (2006.01)
*G01N 13/00* (2006.01)
(Continued)

(52) U.S. Cl.
CPC ........... *G01N 13/00* (2013.01); *G01N 24/081* (2013.01); *G01R 33/448* (2013.01); *G01V 3/175* (2013.01); *G01V 3/18* (2013.01)

(58) Field of Classification Search
CPC .................................................... G01N 13/00
(Continued)

(56) References Cited

U.S. PATENT DOCUMENTS 7,397,240 B2 * 7/2008 Fleury ................ G01N 15/0826
  324/303
10,113,946 B2 * 10/2018 Wickramathilaka ........................
  G01N 15/082
(Continued)

FOREIGN PATENT DOCUMENTS

CN   101915716 A   12/2010
CN   102834737 A   12/2012
(Continued)

OTHER PUBLICATIONS

Office Action and Search Report dated Aug. 1, 2017, for counterpart Chinese patent application No. 201610852977.5.
(Continued)

*Primary Examiner* — Louis M Arana
(74) *Attorney, Agent, or Firm* — Meunier Carlin & Curfman LLC

(57) ABSTRACT

Disclosed herein are methods for testing wettability of tight oil reservoir. The method comprises: by using a nuclear magnetic resonance testing method, testing nuclear magnetic resonance maps of the tight oil reservoir in the saturated water state and in the saturated oil state; by using the nuclear magnetic resonance maps, analyzing a water-wetting degree and an oil-wetting degree of the tight oil reservoir; calculating a mixed wettability index of the tight oil reservoir, and estimating the wettability of the tight oil reservoir according to the mixed wettability index. This disclosure can effectively improve testing efficiency, quantitatively analyze the water-wetting degree and the oil-wetting degree of the tight oil reservoir, and improve accuracy of testing results.

10 Claims, 3 Drawing Sheets

(51) Int. Cl.
  *G01N 24/08* (2006.01)
  *G01R 33/44* (2006.01)
  *G01V 3/18* (2006.01)
  *G01V 3/175* (2006.01)

(58) Field of Classification Search
  USPC .................................................. 324/303, 306
  See application file for complete search history.

(56) References Cited

U.S. PATENT DOCUMENTS

2012/0241149 A1  9/2012  Chen et al.
2016/0334346 A1* 11/2016 Cao Minh ................ G01V 3/32
2018/0088016 A1*  3/2018  Yang ...................... G01V 3/175

FOREIGN PATENT DOCUMENTS

CN       104730587 A    6/2015
CN       104849765 A    8/2015

OTHER PUBLICATIONS

Second Office Action dated Apr. 19, 2018 for counterpart Chinese patent application No. 201610852977.5, along with English translation.

* cited by examiner

METHOD AND DEVICE FOR TESTING WETTABILITY OF DENSE OIL RESERVOIR

TECHNICAL FIELD

The present application relates to the technical field of oil physical property measurement, and in particular to a method and device for testing wettability of tight oil reservoir.

BACKGROUND OF THE DISCLOSURE

In the oil industry, testing of wettability of oil reservoir in rocks is the basis for testing oil physical property, and wettability of tight oil reservoir affects oil-water microcosmic distribution, bound water saturation, residual oil saturation, capillary force and relative permeability and etc. of the reservoir. Accurate testing of the wettability of the tight oil reservoir can help optimization of site development, which has an important guiding role on effective exploitation of the tight oil reservoir.

Currently in the prior art, methods for testing wettability of tight oil reservoir mainly include a contact angle method and a self-absorption method.

The contact angle method mainly includes testing a contact angle of oil and water to a surface of the oil reservoir, estimating an oil-wetting degree and a water-wetting degree of the tight oil reservoir, and then obtaining the wettability of the tight oil reservoir, but this method can only test the wettability of a partial oil reservoir in rocks. As for the tight oil reservoir, the wettability of the partial oil reservoir cannot represent the wettability of the whole oil reservoir.

The self-absorption method is the most widely used method for testing the wettability of the tight oil reservoir in the current, and this method mainly includes measuring and comparing an amount of self-absorbed oil (or self-absorbed water) by a capillary tube and a water displacement oil discharge volume (or an oil displacement water discharge volume) when the oil reservoir is in a residual oil (or bound water) state, and performing a corresponding calculation to obtain the wettability of the oil reservoir. This method can test quantitatively the wettability of the overall oil reservoir. But as for tight oil reservoir, since there are a large amount of micron-sized or even nano-sized air voids in the tight oil reservoir, self-absorption process takes a very long time, usually more than 15 days, and meanwhile it is very difficult to ensure a sufficient self-absorption. In addition, since the air voids in the tight oil reservoir are extremely small, the tight oil reservoir can accommodate an extremely small amount of fluid, so that when the amount of the fluid discharged by self-absorption is measured by a metering tube, it is inevitable to produce a large error, causing a reduction in accuracy of a test result.

The existing techniques contain at least the following defect: the wettability of the overall oil reservoir cannot be tested by the contact angle method. Testing the wettability of tight oil reservoir by the self-absorption method will take a long time, has a low testing efficiency, and meanwhile may produce an inevitable system error, and thus the testing accuracy is low. In addition, the self-absorption method cannot analyze quantitatively the water-wetting degree and the oil-wetting degree of the tight oil reservoir.

SUMMARY OF THE DISCLOSURE

The embodiment of the present application is aimed to provide a method for testing wettability of oil reservoir, to improve the testing efficiency and testing accuracy, and to analyze quantitatively a degree of water-wetting, a degree of oil-wetting and the wettability of the tight oil reservoir without changing original structure of the tight oil reservoir.

In order to solve the above technical problem, an embodiment of the present application provides a method for testing wettability of tight oil reservoir.

The method for testing wettability of tight oil reservoir comprises:

testing nuclear magnetic resonance $T_2$ maps of the tight oil reservoir in a saturated water state and in a saturated oil state;

calculating a water-wetting coefficient and an oil-wetting coefficient of the tight oil reservoir according to the nuclear magnetic resonance $T_2$ maps of the tight oil reservoir in the saturated water state and in the saturated oil state;

calculating a mixed wettability index of the tight oil reservoir by using the water-wetting coefficient and the oil-wetting coefficient of the tight oil reservoir, and determining the wettability of the tight oil reservoir according to the mixed wettability index.

In a preferred embodiment, the process of calculating a water-wetting coefficient and an oil-wetting coefficient of the tight oil reservoir includes:

placing the nuclear magnetic resonance $T_2$ maps of the tight oil reservoir in the saturated water state and in the saturated oil state, into the same coordinate system;

by using a $T_2$ cutoff value, dividing the nuclear magnetic resonance $T_2$ maps in the same coordinate system into left and right sections, wherein the left half section is a nuclear magnetic resonance $T_2$ map of a boundary fluid part;

calculating an amount of bound water and an amount of bound oil in the boundary fluid according to the nuclear magnetic resonance $T_2$ map of the boundary fluid part; and calculating the water-wetting coefficient and the oil-wetting coefficient according to the amount of the bound water and the amount of the bound oil.

In a preferred embodiment, the process of calculating a mixed wettability index of the tight oil reservoir includes:

calculating a difference between the water-wetting coefficient and the oil-wetting coefficient to obtain the mixed wettability index of the tight oil reservoir.

In a preferred embodiment, the process of calculating the amount of the bound water includes:

calculating an area of a region encircled by the nuclear magnetic resonance $T_2$ maps in the saturated water state and in the saturated oil state in the boundary fluid part to obtain the amount of the bound water.

In a preferred embodiment, the process of calculating the amount of the bound oil includes:

calculating an area of a region encircled by the nuclear magnetic resonance $T_2$ map in the saturated oil state and an x-axis in the boundary fluid part to obtain the amount of the bound oil.

In a preferred embodiment, process of calculating the water-wetting coefficient includes:

dividing the amount of the bound water by a sum of the amount of the bound oil and the amount of the bound water to calculate and obtain the water-wetting coefficient.

In a preferred embodiment, the process of calculating the oil-wetting coefficient includes:

dividing the amount of the bound oil by a sum of the amount of the bound oil and the amount of the bound water to calculate and obtain the oil-wetting coefficient.

In a preferred embodiment, the process of calculating the water-wetting coefficient further includes:

dividing the amount of bound oil by a sum of the amount of the bound oil and the amount of the bound water to calculate and obtain the water-wetting coefficient.

In a preferred embodiment, the process of calculating the oil-wetting coefficient further includes:

dividing the amount of the bound water by a sum of the amount of the bound oil and the amount of the bound water to calculate and obtain the oil-wetting coefficient.

In a preferred embodiment, the process of testing nuclear magnetic resonance $T_2$ maps in a saturated water state and in a saturated oil state includes:

taking out a first pillar from the tight oil reservoir;

causing the first pillar to reach the saturated water state, and testing the nuclear magnetic resonance $T_2$ map of the tight oil reservoir in the saturated water state;

after removing a nuclear magnetic signal of water in the first pillar, causing the first pillar to reach the saturated oil state, and testing and obtaining the nuclear magnetic resonance $T_2$ map of the tight oil reservoir in the saturated oil state.

In a preferred embodiment, the process of calculating the $T_2$ cutoff value includes:

taking out a second pillar from the tight oil reservoir;

performing a nuclear magnetic resonance testing under N centrifugal forces on the second pillar, comparing the nuclear magnetic maps to select the centrifugal force, and calculating and obtaining the $T_2$ cutoff value, wherein N≥2.

In a preferred embodiment, the boundary fluid includes fluid bound in the tight oil reservoir, and the bound fluid includes bound water and bound oil.

A device for testing wettability of tight oil reservoir, the device comprising:

an oil reservoir processing module for processing the tight oil reservoir before the testing, and also for changing state of the tight oil reservoir, including causing the tight oil reservoir to reach a saturated water state and a saturated oil state;

a testing module for testing nuclear magnetic resonance $T_2$ maps of the tight oil reservoir in the saturated water state and in the saturated oil state, and also for performing nuclear magnetic resonance testing under N centrifugal forces on the tight oil reservoir, wherein N≥2;

a data calculation module for calculating a $T_2$ cutoff value, and also for calculating a water-wetting coefficient and an oil-wetting coefficient of the tight oil reservoir, and also for calculating a mixed wettability index of the tight oil reservoir;

a data output module for outputting calculation results of the calculated water-wetting coefficient, oil-wetting coefficient and mixed wettability index;

a data analyzing module for analyzing the wettability of the tight oil reservoir according to the output calculation results of the water-wetting coefficient, the oil-wetting coefficient and the mixed wettability index.

In some embodiments, a nuclear magnetic resonance testing method is used for testing the wettability of the tight oil reservoir, which eliminates a self-absorption process of the self-absorption method in the prior art, in which the self-absorption process takes more than 10 days, causing the whole testing to need a long time. In some embodiments, the self-absorption process is eliminated, which shortens testing time and improves testing efficiency. Meanwhile, since air voids in the tight oil reservoir are all submicron-sized or even nano-sized, it is very difficult to achieve a sufficient self-absorption, and the amount of fluid that is discharged through self-absorption is extremely small, so that it is very difficult to accurately measure the amount of fluid that is discharged through self-absorption with a metering tube. All of the above cause an inevitable system error. In some embodiments, it is not necessary to measure the amount of the discharged fluid, and an amount of fluid that is bound in the tight oil reservoir can be measured directly, which reduces errors and improves testing accuracy. In addition, in the prior art, there are lacks of quantitative analysis on the water-wetting degree and the oil-wetting degree of the tight oil reservoir. Whereas in some embodiments, the water-wetting degree and the oil-wetting degree of the tight oil reservoir are quantitatively analyzed by use of the water-wetting coefficient and the oil-wetting coefficient. The present disclosure is to test the wettability of the overall tight oil reservoir, without changing the original microstructure of the tight oil reservoir. Meanwhile, the testing device provided in the embodiment of the disclosure can automatically implement steps of testing wettability of the tight oil reservoir, which does not need specific participation of an implementer, can output testing results directly, thereby simplifying the testing process and improving user experience.

BRIEF DESCRIPTION OF THE DRAWINGS

In order to more clearly explain the embodiment of the present application or the technical solution in the prior art, drawings that need to be used in the embodiments or prior art will be simply introduced below, obviously the drawings in the following description are merely some examples of the present application, for persons ordinarily skilled in the art, it is also possible to obtain other drawings according to these drawings without making creative efforts.

DETAILED DESCRIPTION

The embodiment of the disclosure provides a method for testing wettability of tight oil reservoir.

In the present disclosure, in order to make persons skilled in the art better understand the technical solution of the present application, hereinafter the technical solution in the embodiments of the application will be described clearly and completely incorporating accompanying figures in the embodiments of the application. Obviously, the described embodiments are merely part of embodiments of the application, but not all of the embodiments. On the basis of the embodiment in the application, all of the other embodiments obtained by those skilled in the art in the premise that no creative efforts are made fall within the protection scope of the application.

Figure 1:
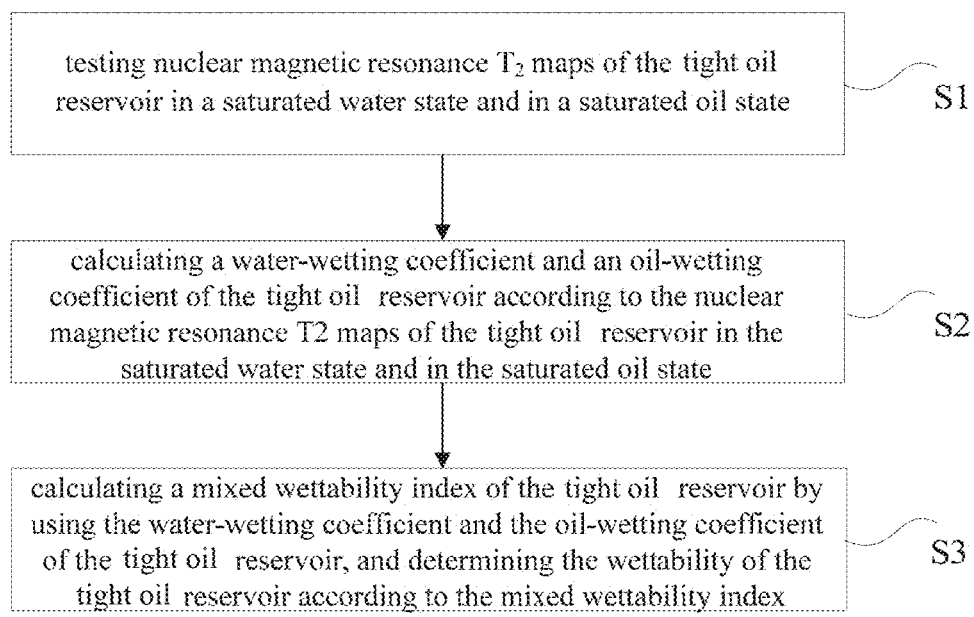
FIG. 1 is an implementation flow chart for illustrating the method for testing wettability of tight oil reservoir according to an embodiment of the disclosure.

FIG. 1 is a method flow chart for illustrating the method for testing wettability of tight oil reservoir as disclosed herein. Although the present application provides operation steps of the method as shown in the following embodiment or drawings, more or less operation steps can be included in the method or device based on the convention or without creative effort. In the steps or structure having no necessary causality logically, execution sequence of these steps or the modular structure of the device is not limited to the execution sequence as shown in the embodiment or drawings of the present application.

Specifically as shown in FIG. 1, an embodiment of the method for testing wettability of tight oil reservoir according to the disclosure can include:

S1: testing nuclear magnetic resonance $T_2$ maps of the tight oil reservoir in a saturated water state and in a saturated oil state.

Figure 3:
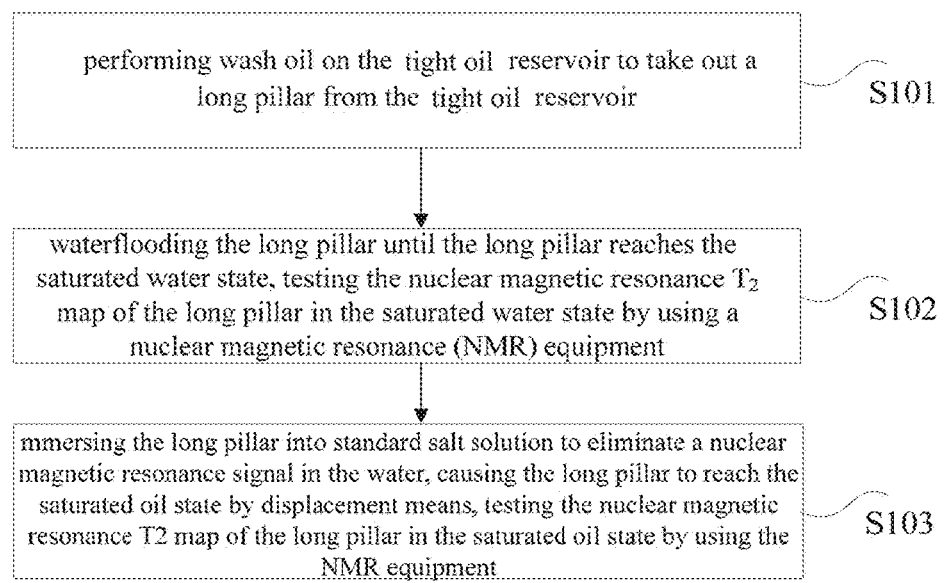
FIG. 3 is a flow chart for illustrating the method for testing nuclear magnetic resonance $T_2$ maps of the tight oil reservoir in the saturated water state and in the saturated oil state according to the embodiment of the disclosure.

Wherein, the testing sequence and testing manner for testing nuclear magnetic resonance $T_2$ maps in the two states can be decided freely by the implementer, for example, the nuclear magnetic resonance $T_2$ map in the saturated water state can be tested at first, or the nuclear magnetic resonance $T_2$ map in the saturated oil state can be tested at first. The flow chart for illustrating the method for testing nuclear magnetic resonance $T_2$ maps of the tight oil reservoir in the saturated water state and in the saturated oil state according to some embodiments is as shown in FIG. 3, specifically including:

S101: performing wash oil on the tight oil reservoir to take out a long pillar from the tight oil reservoir.

In a preferred embodiment of the present application, the selected long pillar may have a length between 5 cm to 7 cm, and a diameter about 2.5 cm.

The long pillar is to be distinguished from a short pillar below for calculating a $T_2$ cutoff value, and for easy understanding is not to define length of the pillar. In addition, here the length and the diameter of the selected long pillar are both optimal values for the purpose of adapting to usual testing conditions. In other embodiments, length, diameter and other parameters of the pillar are not necessary to define, or even a shape of a part of tight oil reservoir being taken out is not necessarily a pillar, but can be other shapes, and these parameters are decided according to the actual testing condition in other embodiments.

Figure 5:
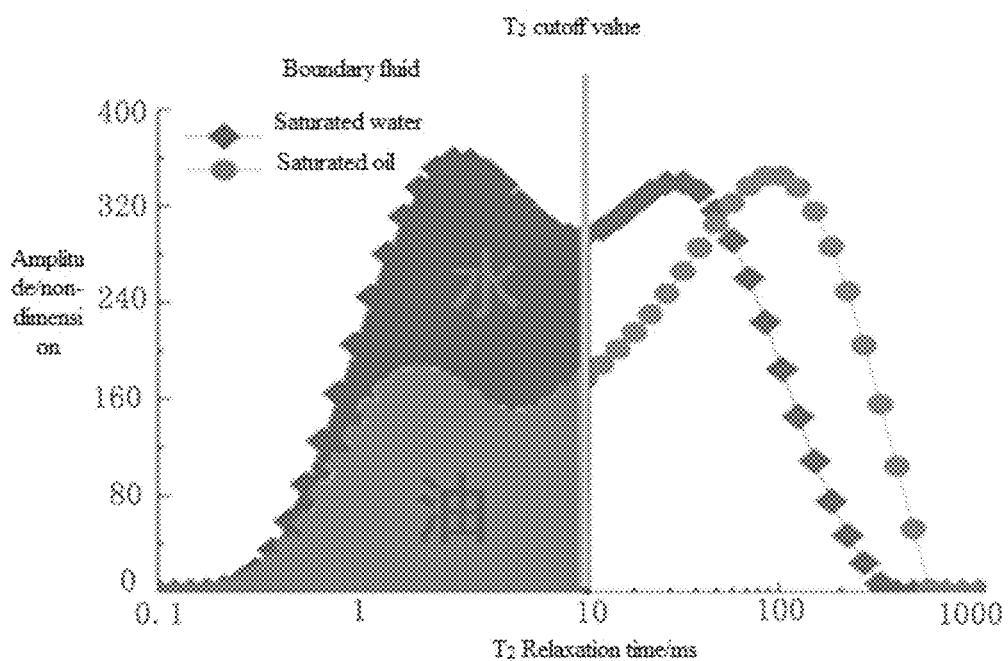
FIG. 5 illustrates the nuclear magnetic resonance $T_2$ maps of the tight oil reservoir in the saturated water state and in the saturated oil state that are obtained according to the embodiment of the disclosure.

S102: waterflooding the long pillar until the pillar reaches the saturated water state, testing the nuclear magnetic resonance $T_2$ map of the long pillar in the saturated water state by using a nuclear magnetic resonance (NMR) equipment to obtain the nuclear magnetic resonance $T_2$ map of the tight oil reservoir in the saturated water state, such as the spectral line corresponding to rhombic dots in FIG. 5.

As for the NMR equipment in this step, there is no specific definition of an equipment for testing the nuclear magnetic resonance $T_2$ maps, or no definition of brands, models and etc. of the equipment. In other embodiments, any nuclear magnetic resonance testing devices can be used as along as it can test the nuclear magnetic resonance $T_2$ maps.

S103: immersing the long pillar into standard salt solution to eliminate a nuclear magnetic resonance signal in the water, causing the pillar to reach the saturated oil state by displacement means, testing the nuclear magnetic resonance $T_2$ map of the long pillar in the saturated oil state by using the NMR equipment to obtain the nuclear magnetic resonance $T_2$ map of the tight oil reservoir in the saturated oil state, such as the spectral line corresponding to circular dots in FIG. 5.

In this step, the displacement means is used for shortening the time required by the long pillar to reach the saturated oil state. In other embodiments, other means can also be employed, for example, water is discharged by oil self-absorption, as long as the long pillar can reach the saturated oil state. The embodiments in which the long pillar reaches the saturated oil state by using other means all belong to other embodiments of the disclosure.

In addition, as for the NMR equipment in this step, there is no specific definition of an equipment for testing the nuclear magnetic resonance $T_2$ maps, or no definition of brands, models and etc. of the equipment. In other embodiments, other nuclear magnetic resonance testing devices can be used as along as it can test the nuclear magnetic resonance maps.

S2: calculating a water-wetting coefficient and an oil-wetting coefficient of the tight oil reservoir according to the nuclear magnetic resonance $T_2$ maps of the tight oil reservoir in the saturated water state and in the saturated oil state.

Figure 4:
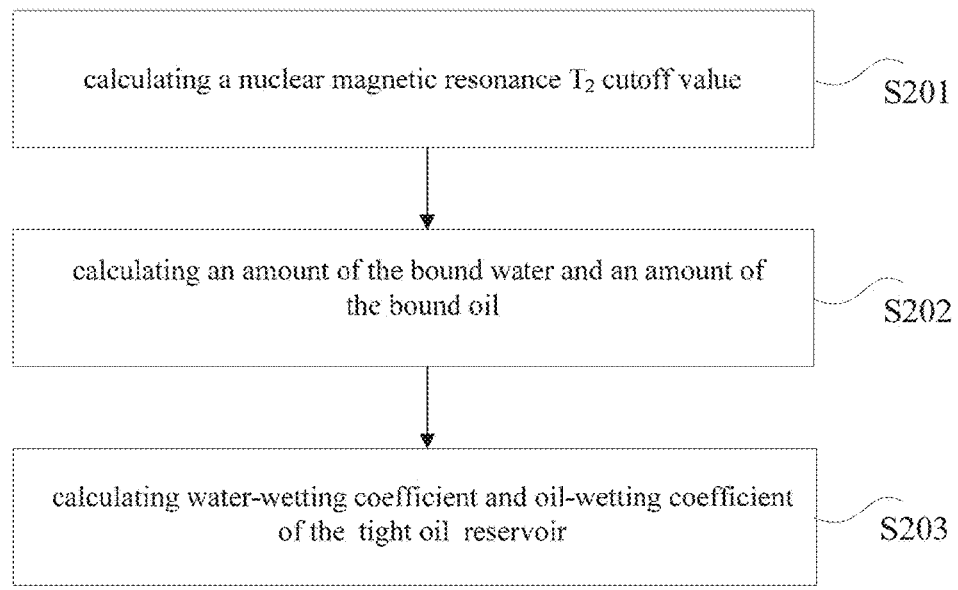
FIG. 4 is a flow chart for illustrating calculation of water-wetting coefficient and oil-wetting coefficient of the tight oil reservoir according to the embodiment of the disclosure.

The water-wetting coefficient and the oil-wetting coefficient are mainly used for measuring the water-wetting degree and the oil-wetting degree of the tight oil reservoir. FIG. 4 is a flow chart for illustrating calculation of water-wetting coefficient and oil-wetting coefficient of the tight oil reservoir according to the embodiment of the disclosure, specifically including:

S201: calculating a nuclear magnetic resonance $T_2$ cutoff value.

A short pillar having a length of 2 to 3 cm and a diameter of about 2.5 cm is taken out from the tight oil reservoir after the wash oil in the S1.

The short pillar described in this step is to be distinguished from the long pillar for testing the nuclear magnetic resonance $T_2$ maps, and for easy understanding is not to define a length of the pillar. In addition, here the length and the diameter of the selected short pillar are both optimal values for the purpose of adapting to usual testing conditions. In other embodiments, length, diameter and other parameters of the pillar are not necessary to define, or even a shape of a part of tight oil reservoir being taken out is not necessarily a pillar, but can be other shapes, and these parameters are decided according to the actual testing condition in other embodiments.

Waterflooding the short pillar until the short pillar reaches the saturated water state, performing the nuclear magnetic resonance testing under N centrifugal forces on the short pillar in the saturated water state, comparing the nuclear magnetic maps to select the centrifugal forces and calculate the $T_2$ cutoff value, wherein N≥2.

In this step, the described waterflooding is aimed to make the long pillar reach the saturated water state. In other embodiments, the oil injection can be performed by self-absorption or displacement means, or other means.

This step belongs to a conventional technical means, and in other embodiments, the implementer of the method can decide a specific testing method according to the actual situation, with the purpose of calculating the $T_2$ cutoff value.

S202: calculating an amount of the bound water and an amount of the bound oil.

Wherein, the bound water and the bound oil generally refer to water and oil that are bound in the oil reservoir. In an embodiment of the present application, the process of calculating the amount of the bound water and the amount of the bound oil can include:

S2021: placing the nuclear magnetic resonance $T_2$ maps of the tight oil reservoir in the saturated water state and in the saturated oil state, into the same coordinate system, dividing the maps into left and right sections by using the $T_2$ cutoff value, as shown in FIG. 5, the left half section is a boundary fluid part, the boundary fluid refers to the fluid that is bound by the tight oil reservoir, including the bound water and the bound oil.

S2022: calculating an area of a region encircled by the nuclear magnetic resonance $T_2$ maps in the saturated water state and in the saturated oil state in the boundary fluid part (as shown in the black region marking water in FIG. 5), to obtain the amount of the bound water.

S2023: calculating an area of a region encircled by the nuclear magnetic resonance $T_2$ map in the saturated oil state and an x-axis in the boundary fluid part (as shown in the gray region marking oil in FIG. 5) to obtain the amount of the bound oil.

In specific implementation process of S2022 and S2023, region colors and marking methods are not necessarily limited to the drawing, and other colors and other marking methods can also be employed, as long as the regions corresponding to the bound water and the bound oil can be clearly distinguished.

S203: calculating water-wetting coefficient and oil-wetting coefficient of the tight oil reservoir.

In some embodiments, the amount of the bound water and the amount of the bound oil are added together to calculate and obtain a total amount of the boundary fluid; dividing the amount of the bound water by the total amount of the boundary fluid to calculate and obtain the water-wetting coefficient of the tight oil reservoir; dividing the amount of the bound oil by the total amount of the boundary fluid to calculate and obtain the oil-wetting coefficient of the tight oil reservoir.

The method for calculating the oil-wetting coefficient and the water-wetting coefficient employed in this step is mainly for conforming to normal logical custom. In other embodiments, it is practicable to divide the amount of the bound water by the total amount of the boundary fluid to obtain the oil-wetting coefficient of the tight oil reservoir; similarly, it is also practicable to divide the amount of the bound oil by the total amount of the boundary fluid to obtain the water-wetting coefficient of the tight oil reservoir.

The water-wetting degree of the tight oil reservoir can be quantitatively analyzed by using the water-wetting coefficient, and the oil-wetting degree of the tight oil reservoir can be quantitatively analyzed by using the oil-wetting coefficient.

S3: calculating a mixed wettability index of the tight oil reservoir by using the water-wetting coefficient and the oil-wetting coefficient of the tight oil reservoir, and determining the wettability of the tight oil reservoir according to the mixed wettability index.

The mixed wettability index itself can directly determine the wettability of the tight oil reservoir. Also, the wettability of the tight oil reservoir can be divided into different types according to a value range of the mixed wettability index, and the wettability of the tight oil reservoir can be determined according to the type to which the wettability belongs. The specific dividing manner is not necessary to define.

In some embodiments, the specific calculation may include:

S301: subtracting the oil-wetting coefficient from the water-wetting coefficient to obtain the mixed wettability index of the tight oil reservoir.

In other embodiments, it is also practicable to subtract the water-wetting coefficient from the oil-wetting coefficient to obtain the mixed wettability index of the tight oil reservoir. In some embodiments, a difference between the water-wetting coefficient and the oil-wetting coefficient is used for defining the mixed wettability index of the tight oil reservoir. In other embodiments, other defining manner can also be employed, for example, it is practicable to divide the water-wetting coefficient by the oil-wetting coefficient to obtain the mixed wettability index of the tight oil reservoir; or it is also practicable to divide the oil-wetting coefficient by the water-wetting coefficient to obtain the mixed wettability index of the tight oil reservoir.

S302: determining wettability of the tight oil reservoir according to the mixed wettability index of the tight oil reservoir.

The determining wettability of the tight oil reservoir can be regarded as determining the type of the wettability of the tight oil reservoir. In an embodiment, according to the value range of the mixed wettability index of the tight oil reservoir, the wettability of the tight oil reservoir is divided into seven types, including: strong oil-wetting, oil-wetting, weak oil-wetting, neutral, weak water-wetting, water-wetting and strong water-wetting. Specific corresponding relationship between the value range of the mixed wettability index and the type of the wettability is as shown in Table 1.

TABLE 1

| | Type of wettability of dense oil reservoir | | | | | | |
|---|---|---|---|---|---|---|---|
| wettability of rocks | strong oil-wetting | oil-wetting | weak oil-wetting | neutral | weak water-wetting | water-wetting | strong water-wetting |
| mixed wettability index | −1.0~ −0.70 | −0.70~ −0.30 | −0.30~ −0.10 | −0.10~0.10 | 0.10~0.30 | 0.30~0.70 | 0.70~1.0 |

The type in table 1 is to be consistent with the type in conventional methods, and in specific implementation of other embodiments, it is not necessary to limit the type to such manner. For example, it is practicable to define the type of wettability of the tight oil reservoir whose mixed wettability index is within the range of −0.1 to −0.70 to be "strong oil-wetting", and it is practicable to define the type of wettability of the tight oil reservoir whose wettability index is within the range of 0.70 to 1.0 to be "strong water-wetting", In addition, the manners of dividing the wettability type of the tight oil reservoir on the basis of other mixed wettability indexes or on the basis of other indexes similar to the calculation of the mixed wettability index in this embodiment all belong to some embodiments of the disclosure.

In the above embodiment of the disclosure, the self-absorption process of the self-absorption method in the prior art is eliminated, which shortens the testing time and improves the testing efficiency. In some embodiments, a nuclear magnetic resonance testing technique can be used to directly measure an amount of fluid that is bound in the tight oil reservoir without having to measure an amount of the discharged fluid, which reduces errors and improves testing accuracy.

In addition, in some embodiments, the water-wetting coefficient and the oil-wetting coefficient are used for quantitatively analyzing the water-wetting degree and the oil-wetting degree of the tight oil reservoir, which solves the problem in the prior art that there lacks of quantitative analysis on the water-wetting degree and the oil-wetting degree of the tight oil reservoir; indicators for quantitatively estimating the wettability of the tight oil reservoir are established, and the types of wettability of the tight oil reservoir are divided by the mixed wettability index of the tight oil reservoir.

The embodiments of the present disclosure is to test wettability of the overall tight oil reservoir, and meanwhile not change the original microstructure of the tight oil reservoir.

Table 2 shows testing results of the wettability of 10 kinds of tight oil reservoir in the embodiment, including water-wetting coefficients and oil-wetting coefficients of 10 kinds of tight oil reservoir, and the wettability of 10 kinds of tight oil reservoir is also tested by the self-absorption method, and testing results of the self-absorption method are compared with the results obtained in this embodiment. The AI indexes described in the table are namely indicators for estimating wettability of the tight oil reservoir in the self-absorption, it can be seen by comparison that, there is a very good corresponding relationship between the mixed wettability indexes obtained through testing in the embodiment of the disclosure and the AI indexes, which in fact proves reliability of the present disclosure. Meanwhile, it can be seen through theoretical analysis that, in the embodiments of the disclosure, system errors caused in the self-absorption method can be avoided, therefore the accuracy of the testing results obtained in the disclosure is higher than the self-absorption method. In addition, in the embodiments of the disclosure, testing the wettability of one tight oil reservoir takes 1.5 days, while testing the wettability of one tight oil reservoir by the self-absorption method generally takes 15 days or longer time. Compared with the self-absorption method, the embodiment of the disclosure shortens the testing time.

TABLE 2

Testing results of wettability of 10 kinds of dense oil reservoir

| Tight oil reservoir | AI index | Mixed wettability index | Water-wetting coefficient | Oil-wetting coefficient | Wettability of rocks |
|---|---|---|---|---|---|
| 1 | −0.58 | −0.82 | 0.24 | 0.76 | Strong oil-wetting |
| 2 | −0.55 | −0.57 | 0.21 | 0.79 | Oil-wetting |
| 3 | −0.45 | −0.37 | 0.32 | 0.68 | Oil-wetting |
| 4 | −0.42 | −0.32 | 0.34 | 0.66 | Oil-wetting |
| 5 | −0.40 | −0.56 | 0.22 | 0.78 | Oil-wetting |
| 6 | −0.31 | −0.62 | 0.19 | 0.81 | Oil-wetting |
| 7 | −0.24 | −0.20 | 0.4 | 0.6 | Weak oil-wetting |
| 8 | 0.16 | 0.11 | 0.61 | 0.39 | Weak water-wetting |
| 9 | 0.27 | 0.44 | 0.73 | 0.27 | Weak water-wetting |
| 10 | 0.36 | 0.59 | 0.79 | 0.21 | Water-wetting |

Other embodiments of the present disclosure are not necessary to be limited to the above implementing steps, for example, as for the S1 of testing nuclear magnetic resonance $T_2$ maps of the tight oil reservoir in the saturated water state and in the saturated oil state and the S2 of calculating the $T_2$ cutoff value, there is no sequential order of the steps S1 and S2. In other embodiments, the $T_2$ cutoff value can be calculated at first, and then the nuclear magnetic resonance $T_2$ maps of the tight oil reservoir in the saturated water state and in the saturated oil state are tested. For another example, as for the steps S102 and S103, in other embodiments, specific implementation further includes:

S102: oiling the long pillar until the long pillar reaches the saturated oil state, testing the nuclear magnetic resonance $T_2$ map of the long pillar in the saturated oil state by using a nuclear magnetic resonance (NMR) equipment to obtain the nuclear magnetic resonance $T_2$ map of the tight oil reservoir in the saturated oil state.

In this step, the described oiling is aimed to make the long pillar reach the saturated oil state, and in other embodiments of the disclosure, the oiling can be performed by self-absorption or displacement means, or other means.

As for the NMR equipment in this step, there is no specific definition of an equipment for testing the nuclear magnetic resonance $T_2$ maps, or no definition of brands, models and etc. of the equipment. In other embodiments of the disclosure, any nuclear magnetic resonance testing devices can be used as along as it can test the nuclear magnetic resonance $T_2$ maps.

S103: causing the long pillar to reach the saturated water state by displacement means, testing the nuclear magnetic resonance $T_2$ map of the long pillar in the saturated oil state by using a nuclear magnetic resonance (NMR) equipment to obtain the nuclear magnetic resonance $T_2$ map of the tight oil reservoir in the saturated water state.

In this step, the displacement means is used for shortening the time required by the long pillar to reach the saturated water state. In other embodiments of the disclosure, other means can also be employed, for example, oil is discharged by water self-absorption, as long as the long pillar can reach the saturated water state. The embodiments in which the long pillar reaches the saturated water state by using other means all belong to other embodiments of the disclosure.

In addition, as for the NMR equipment in this step, there is no specific definition of an equipment for testing the nuclear magnetic resonance $T_2$ maps, or no definition of brands and models of the equipment. In other embodiments of the disclosure, any nuclear magnetic resonance testing devices can be used as along as it can test the nuclear magnetic resonance $T_2$ maps.

Figure 2:
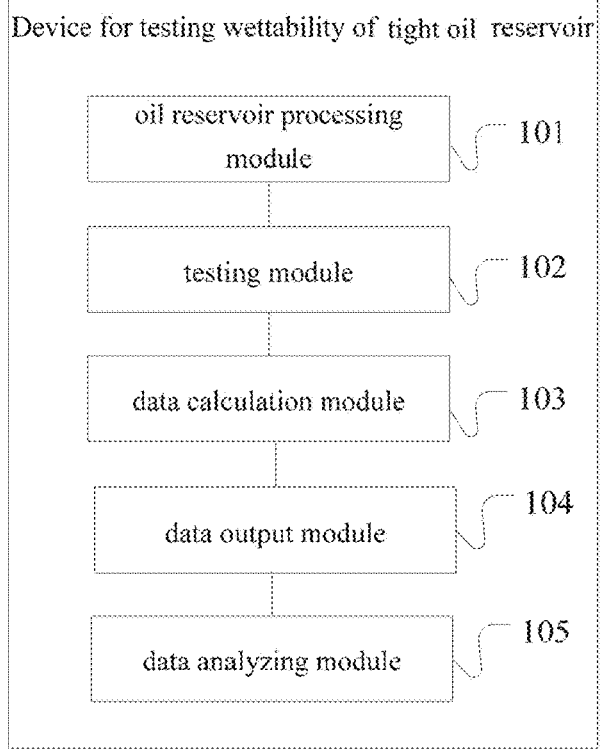
FIG. 2 is a schematic diagram for illustrating modular structure of the device for testing wettability of tight oil reservoir according to the embodiment of the disclosure.

Based on the method for testing wettability of the tight oil reservoir as described herein, the disclosure provides a device for testing wettability of the tight oil reservoir. The device can be used for automatically implementing the method in the testing process. FIG. 2 is a schematic diagram for illustrating the modular structure of an example of the device for testing wettability of the tight oil reservoir according to the disclosure, as shown in FIG. 2, the device may include:

an oil reservoir processing module 101 for processing the tight oil reservoir before the testing, and also for changing the state of the tight oil reservoir, including causing the tight oil reservoir to reach a saturated water state and a saturated oil state:

a testing module 102 for testing nuclear magnetic resonance $T_2$ maps of the tight oil reservoir in the saturated water state and in the saturated oil state, and also for performing nuclear magnetic resonance testing under different centrifugal forces on the tight oil reservoir;

a data calculation module 103 for calculating a $T_2$ cutoff value, and also for calculating a water-wetting coefficient and an oil-wetting coefficient of the tight oil reservoir, and also for calculating a mixed wettability index of the tight oil reservoir;

a data output module 104 for outputting calculation results of the calculated water-wetting coefficient, oil-wetting coefficient and mixed wettability index;

a data analyzing module 105 for analyzing wettability of the tight oil reservoir according to the output calculation results of the water-wetting coefficient, the oil-wetting coefficient and the mixed wettability index.

The above embodiment provides a device for testing wettability of the tight oil reservoir, by which the whole testing process can be performed automatically, thereby making the testing process be more simple and rapid.

It can be seen from description of the above embodiment that, persons skilled in the art can clearly know that the present disclosure can rapidly test wettability of the tight oil reservoir, and the accuracy is high, and meanwhile the water-wetting degree and the oil-wetting degree of the tight oil reservoir can be quantitatively analyzed.

Of course, the present disclosure can not only test wettability of the tight oil reservoir, wettability of the other non-tight oil reservoir can also be tested by the method for testing wettability of tight oil reservoir. The embodiments in which the method for testing wettability of tight oil reservoir provided by the disclosure is used for testing wettability of non-tight oil reservoir all belong to other embodiments of the disclosure.

The embodiments of the disclosure are described in a progressive manner, the same or similar parts in the embodiments are for reference to each other, and emphasis in each embodiment is the difference from other embodiments.

Although the contents of the disclosure describes different manners of testing wettability of tight oil reservoir, various time sequences for testing nuclear magnetic resonance maps of the tight oil reservoir, calculating the water-wetting coefficient and the oil-wetting coefficient, calculating the mixed wettability index of the tight oil reservoir and determining wettability of the tight oil reservoir, and includes description of data acquisition/processing/output manners and the like, the present application is not limited to have to be industrial standard or the situation described in the embodiment, or the like, and expectable implementation effects that are the same as, equivalent to or similar to or by deformation of the above embodiment can also be achieved by certain industrial standards or by user-defined manners or by an implementation solution obtained by slightly amending the implementation described in the embodiment. Embodiments in which these amended or deformed data acquisition, processing, outputting and judging manners are applied can still fall within the scope of available implementation solutions of the present application.

Although the present application provides operation steps of the method as described in the embodiment or the flow charts, more or less operation steps can be included based on the conventional or non-creative means. The sequence of steps listed in the embodiment is merely one of various execution sequences of the steps, but does not represent unique execution sequence. In the actual execution of a device or client product, it is practicable to perform sequential execution or parallel execution according to the method shown in the embodiment or the drawing (such as a parallel processor or an environment of multithread processing, or even a distributive data processing environment). The terms "include", "contain" or any other variants thereof that are aimed to cover non-exclusive including, makes the process, methods, products or devices including a series of elements not only include those elements but also include other elements that are not clearly listed, or further include elements that are inherent to the process, methods, products or devices. Without more limitation, it is not exclusive that there are additional same or equivalent elements in the process, methods, products or devices including the elements.

The modules and devices and etc. illustrated in the above embodiment can specifically be implemented by a computer chip or an entity, or by a product having a certain function. For convenience of description, the above devices are described by being divided into various modules by functions. Of course, in implementation of the present application, the functions of the modules can be realized in the same one or multiple softwares and/or hardwares, or the module for realizing the same one function can be achieved by combining multiple sub modules or sub units. The embodiment of the above-described device is merely schematic, for example, the division of the units is merely a logically functional division, and there may be other division manners in actual implementation, for example multiple units or components can be combined or integrated into another system, or some features can be ignored or not executed.

It is also known to persons skilled in the art that, except that a controller is realized purely by computer readable program codes, it is absolutely possible that the controller realizes the same function with a logic gate, a switch, an application-specific integrated circuit, a programmable logic controller and an embedded microcontroller and the like by logically programming the method steps. Therefore such controller can be regarded as a hardware component, and devices therein for realizing various functions can also be regarded as structure within the hardware component. Or even, the devices for realizing various functions can be regarded as software modules that implement the method or as structure within the hardware component.

It can be seen from the description of the above embodiment, persons skilled in the art can clearly know that the present application can be implemented by means of software in combination with necessary general hardware platform. Based on such understanding, the substantive technical solution or the portions of the application that make contribution to the prior art can be embodied in the form of software products, the computer software product can be stored in a storage media, such as ROM/RAM, a disc, an optical disc or the like, including several instructions to make a computer device (which can be a personal computer, a mobile terminal, a server or a network device or the like) execute the method described in the embodiments or some parts of the embodiments of the present application.

The embodiments of the disclosure are described in a progressive manner, the same or similar parts in the embodiments are for reference to each other, and emphasis in each embodiment is the difference from other embodiments. The present application can be applied in numerous general or specific-purpose computer system environment or configuration, such as a personal computer, a server computer, a handheld device or a portable device, a tablet device, a multi-processor system, a microprocessor-based system, a set-top box, a programmable electronic device, a network PC, a small-size computer, a large-scale computer, distributed computing environment including the above-described any systems or device, and the like.

Although the present application has been described by embodiments, persons ordinarily skilled in the art know that, the present application may have many variations and changes without departing from the spirit of the application, and it is desirable that the attached claims include these variations and changes without departing from the spirit of the application.

What is claimed is:

1. A method for testing wettability of a tight oil reservoir, the method comprising:
    testing nuclear magnetic resonance $T_2$ maps of the tight oil reservoir in a saturated water state and in a saturated oil state;
    calculating a water-wetting coefficient and an oil-wetting coefficient of the tight oil reservoir according to the nuclear magnetic resonance T2 maps of the tight oil reservoir in the saturated water state and in the saturated oil state;
    calculating a mixed wettability index of the tight oil reservoir by using the water-wetting coefficient and the oil-wetting coefficient of the tight oil reservoir, and determining the wettability of the tight oil reservoir according to the mixed wettability index;
    wherein calculating a mixed wettability index of the tight oil reservoir includes:
        calculating a difference between the water-wetting coefficient and the oil-wetting coefficient to obtain the mixed wettability index of the tight oil reservoir,
    wherein calculating a water-wetting coefficient and an oil-wetting coefficient of the tight oil reservoir includes:
        placing the nuclear magnetic resonance T2 maps of the tight oil reservoir in the saturated water state and in the saturated oil state, into the same coordinate system;
        by using a T2 cutoff value, dividing the nuclear magnetic resonance T2 maps in the same coordinate system into left and right sections, wherein the left half section is a nuclear magnetic resonance T2 map of a boundary fluid part;
        calculating an amount of bound water and an amount of bound oil in the boundary fluid according to the nuclear magnetic resonance T2 map of the boundary fluid part; and
        calculating the water-wetting coefficient and the oil-wetting coefficient according to the amount of the bound water and the amount of the bound oil;
    wherein testing nuclear magnetic resonance T2 maps in a saturated water state and in a saturated oil state includes:
        taking out a first pillar from the tight oil reservoir;
        causing the first pillar to reach the saturated water state, and testing the nuclear magnetic resonance T2 map of the tight oil reservoir in the saturated water state; and
        after removing a nuclear magnetic signal of water in the first pillar, causing the first pillar to reach the saturated oil state, and testing the nuclear magnetic resonance T2 map of the tight oil reservoir in the saturated oil state.

2. The method for testing wettability of the tight oil reservoir according to claim 1, wherein calculating the amount of the bound water includes:
    calculating an area of a region encircled by the nuclear magnetic resonance T2 maps in the saturated water state and in the saturated oil state in the boundary fluid part to obtain the amount of the bound water.

3. The method for testing wettability of the tight oil reservoir according to claim 1, wherein calculating the amount of the bound oil includes:
    calculating an area of a region encircled by the nuclear magnetic resonance T2 map in the saturated oil state and an x-axis in the boundary fluid part to obtain the amount of the bound oil.

4. The method for testing wettability of the tight oil reservoir according to claim 1, wherein calculating the water-wetting coefficient includes:
    dividing the amount of bound water by a sum of the amount of bound oil and the amount of bound water to calculate and obtain the water-wetting coefficient.

5. The method for testing wettability of the tight oil reservoir according to claim 1, wherein calculating the oil-wetting coefficient includes:
    dividing the amount of bound oil by a sum of the amount of bound oil and the amount of bound water to calculate and obtain the oil-wetting coefficient.

6. The method for testing wettability of the tight oil reservoir according to claim 1, wherein calculating the water-wetting coefficient includes:
    dividing the amount of bound oil by a sum of the amount of bound oil and the amount of bound water to calculate and obtain the water-wetting coefficient.

7. The method for testing wettability of the tight oil reservoir according to claim 1, wherein calculating the oil-wetting coefficient includes:
    dividing the amount of bound water by a sum of the amount of bound oil and the amount of bound water to calculate and obtain the oil-wetting coefficient.

8. The method for testing wettability of the tight oil reservoir according to claim 1, wherein the process of calculating the $T_2$ cutoff value includes:
    taking out a second pillar from the tight oil reservoir;
    performing nuclear magnetic resonance testing under N centrifugal forces on the second pillar, comparing the nuclear magnetic maps to select the centrifugal forces and calculate the $T_2$ cutoff value, wherein N≥2.

9. The method for testing wettability of the tight oil reservoir according to claim 1, wherein the boundary fluid includes fluid bound in the tight oil reservoir, and the bound fluid includes bound water and bound oil.

10. A device for testing wettability of the tight oil reservoir, the device comprising:
    an oil reservoir processing module for tight the tight oil reservoir before the testing, and also for changing a state of the tight oil reservoir, including causing the tight oil reservoir to reach a saturated water state and a saturated oil state;

a testing module for testing nuclear magnetic resonance $T_2$ maps of the tight oil reservoir in the saturated water state and in the saturated oil state, and also for performing nuclear magnetic resonance testing under N centrifugal forces on the tight oil reservoir, wherein $N \geq 2$;

a data calculation module for calculating a $T_2$ cutoff value, and also for calculating a water-wetting coefficient and an oil-wetting coefficient of the tight oil reservoir, and also for calculating a mixed wettability index of the tight oil reservoir, wherein calculating a mixed wettability index of the tight oil reservoir includes: calculating a difference between the water-wetting coefficient and the oil-wetting coefficient to obtain the mixed wettability index of the tight oil reservoir;

a data output module for outputting calculation results of the calculated water-wetting coefficient, oil-wetting coefficient and mixed wettability index; and a data analyzing module for analyzing the wettability of the tight oil reservoir according to the output calculation results of the water-wetting coefficient, the oil-wetting coefficient and the mixed wettability index.

\* \* \* \* \*